(12) United States Patent
Moore et al.

(10) Patent No.: US 8,147,407 B2
(45) Date of Patent: Apr. 3, 2012

(54) SENSOR KITS FOR SLEEP DIAGNOSTIC TESTING

(75) Inventors: James Patrick Moore, Bloomington, MN (US); Evan Stuart Johnston, Blaine, MN (US); Terry Joseph Lerach, Saint Michael, MN (US)

(73) Assignee: Dymedix Corporation, Shoreview, MN (US)

( * ) Notice: Subject to any disclaimer, the term of this patent is extended or adjusted under 35 U.S.C. 154(b) by 378 days.

(21) Appl. No.: 12/547,167

(22) Filed: Aug. 25, 2009

(65) Prior Publication Data

US 2010/0056882 A1    Mar. 4, 2010

Related U.S. Application Data

(60) Provisional application No. 61/092,448, filed on Aug. 28, 2008.

(51) Int. Cl.
*A61B 5/00* (2006.01)

(52) U.S. Cl. ........ 600/301; 600/509; 600/534; 600/538; 600/544

(58) Field of Classification Search .................. 600/301, 600/509
See application file for complete search history.

(56) References Cited

U.S. PATENT DOCUMENTS

| | | | |
|---|---|---|---|
| 5,311,875 A | 5/1994 | Stasz | |
| 6,059,111 A * | 5/2000 | Davila et al. | 206/438 |
| 6,254,545 B1 | 7/2001 | Stasz | |
| 6,306,088 B1 * | 10/2001 | Krausman et al. | 600/301 |
| 6,485,432 B1 | 11/2002 | Stasz | |
| 6,491,642 B1 | 12/2002 | Stasz | |
| 6,894,427 B2 | 5/2005 | Alfini | |
| 2007/0012089 A1 | 1/2007 | Stasz | |
| 2007/0106167 A1 * | 5/2007 | Kinast | 600/509 |

* cited by examiner

*Primary Examiner* — Melanie Hand
(74) *Attorney, Agent, or Firm* — Nikolai & Mersereau, P.A.; Thomas J. Nikolai

(57) ABSTRACT

System for storing pre-packaged sleep related sensors and facilitating effective, efficient, or error-free usage of the sleep related sensors for sleep diagnostic testing including a thoracic respiratory effort belt, an abdominal effort belt, an oxygen saturation sensor, and a nasal and oral airflow sensor, a receptacle for storing sleep-related sensors, and instruction for using the sleep-related sensors.

20 Claims, 5 Drawing Sheets

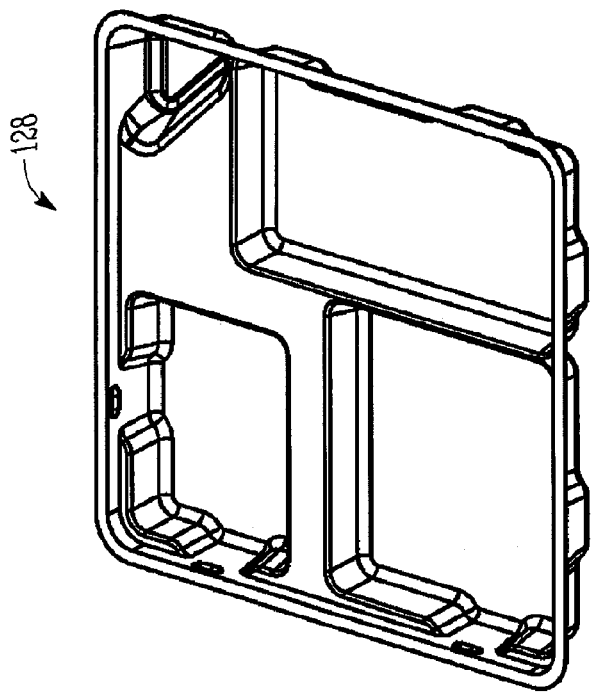
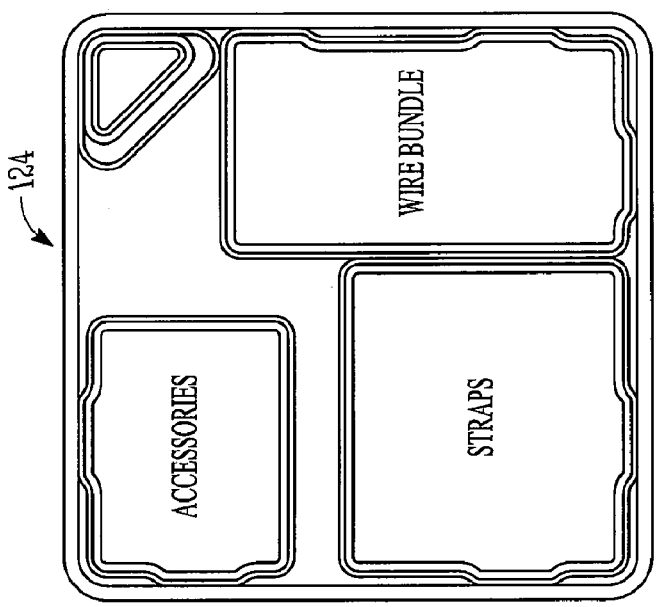
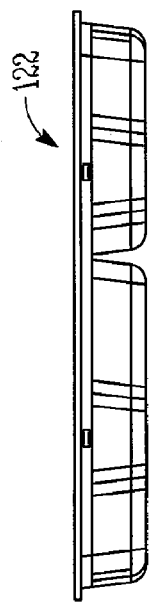
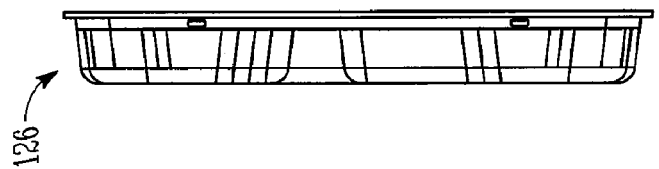
FIG. 5D
FIG. 5A
FIG. 5B
FIG. 5C

SENSOR KITS FOR SLEEP DIAGNOSTIC TESTING

CLAIM OF PRIORITY

This patent application claims the benefit of priority to U.S. Provisional Patent Application Ser. No. 61/092,448, filed on Aug. 28, 2008, which application is herein incorporated by reference in its entirety.

TECHNICAL FIELD

The present subject matter relates generally to the field of neurological disorders and more specifically to the area of sleep medicine and yet even more specifically to the area of sleep diagnosis for patients who suffer from sleep disorders. More particularly, the present subject matter relates to sensor kits for sleep diagnostic testing.

BACKGROUND

Sleep disorders have recently become the focus of a growing number of physicians. Sleep disorders include obstructive sleep apnea, central sleep apnea, complex sleep apnea, snoring, restless leg syndrome (RLS), periodic limb movement (PLM), sudden infant death syndrome (SIDS), and related neurological and physiological events or conditions occurring during sleep. Many hospitals and clinics have established sleep laboratories (sleep labs) to diagnose and treat sleep disorders. In the sleep laboratories, practitioners use instrumentation to monitor and record a patient's sleep states, stages and behaviors during sleep. Practitioners rely on these recordings to diagnose patients and prescribe proper therapies.

A goal of addressing sleeping disorders is to help a person sleep better. Another goal of addressing sleeping disorders is to help a person live longer. It is well known that various undesirable behaviors often occur during sleep such as snoring, apnea episodes, abnormal breathing episodes, Bruxism (teeth clenching and grinding) and the like. It is further known that these disorders and other undesirable behaviors can not only lead to insufficient amounts of sleep or fatigue but are also linked to co-morbidities such as obesity, diabetes, cardiac diseases, stroke and SIDS, all of which lead to a premature death. Serious efforts are being made to reduce or eliminate these undesirable disorders and behaviors in part because of these co-morbidity concerns.

SUMMARY

The present subject matter provides a means for a clean and convenient method to use a pre-arranged and pre-packaged, disposable or reusable sensor kit for the home or the sleep laboratory setting.

Historically, sleep studies have been done in sleep labs or sleep clinics. There has been a predisposition to using reusable sensor because of the cost factor. Some labs have decided to use disposable sensors because of infection control and the ease of no cleaning between tests.

Efforts continue to use home testing or at least home screening instead of making the patient come in to a sleep lab facility for an overnight study. There are many good reasons for home studies. First, it is less expensive in that hospital costs are avoided. Secondly, it is easier to get patients to agree to get a study done in their own homes and many patients are unable, for one reason or another, to come to the clinic or lab.

It is believed that clinic and patients will be receptive to using disposable sensors for home studies. Use of disposable sensors and electrodes relieve patient concerns about reusable sensors and electrodes, including concerns of who may have used the sensors and electrodes last, or who may have cleaned them, and how well they were cleaned.

It has been determined by the American Academy of Sleep Medicine (AASM) that there will be four different levels of portable home studies. Each may require a different suite of equipment that will record different kinds of data to be evaluated and each of the four levels will require different electrodes/sensors. Level I is the most detailed and is identical to what is done in a hospital or clinic sleep center with a variety of polysomnograph (PSG) machines. Levels II, III and IV require recording less and less data in descending order.

Level I or Type I testing is what is generally accepted as an attended standard polysomnography (PSG) test with a minimum of seven parameters observed and measured, including:
 1. Electrooculogram (EOG)
 2. Electroencephalogram (EEG)
 3. Electrocardiogram (ECG)
 4. Electromyogram (EMG)
 5. Airflow
 6. Respiratory Effort
 7. Oxygen Saturation In certain examples, a sleep practitioner/technician is required to be in constant attendance during testing.

Level II or Type II testing is referred to as testing with devices that are comprehensive and portable and that measure the same channels as Type I testing, except that a heart-rate monitor may replace the electrocardiogram and a sleep practitioner is not necessarily in constant attendance.

Level III or Type III testing encompasses devices that have a minimum of four sensor channels monitored, including ventilation or airflow (at least two channels of respiratory movement, or respiratory movement and airflow), heart rate or ECG, and oxygen saturation.

Level IV or Type IV testing involves testing with devices that continuously monitor one or two parameters, typically airflow and or oxygen saturation.

Applicants have devised specialized disposable kits loaded with the sensors and electrodes each patient will need for the home study for each level of testing or screening the patient will be doing. It is expected that the technician conducting the test will provide the non-disposable electronic equipment, such as the ECG machine, the pulse oxymeter, the EEG machine and the electronic fetal monitoring (EFM) machine that may be required for each study.

A feature of the present subject matter includes providing disposable components that comes in contact with the patient, e.g., the sensors and electrodes.

There is a need to provide a sleep practitioner with a variety of Type I, Type II, Type III and Type IV sensor kits that contain sleep related sensors that are pre-packaged in a sterile, compartmental tray or sealed pouch with appropriate ID markings to facilitate error-free usage.

There is a need to provide a sleep practitioner with a variety of Type I, Type II, Type III and Type IV sensor kits that contains sleep related sensors/electrodes that are pre-arranged.

There is a need to provide a sleep practitioner with a variety of Type I, Type II, Type III and Type IV sensor kits that contains sleep related sensors/electrodes that are clean, new and unused.

There is a need to provide a sleep practitioner with a variety of Type I, Type II, Type III and Type IV sensor kits that contains sleep related sensors/electrodes that are sterile.

There is a need to provide a sleep practitioner with a variety of Type I, Type II, Type III and Type IV sensor kits that contains sleep related sensors/electrodes that are reusable.

There is a need to provide a sleep practitioner with a variety of Type I, Type II, Type III and Type IV sensor kits that contain a multitude of various connector terminations to interface with the different commercially available PSG type devices that are presently used in sleep laboratories and that may also be used for home testing.

There is also a need to provide a sleep practitioner with a variety of Type I, Type II, Type III and Type IV sensor kits that contain sleep related sensors/electrodes that are disposable rather than reusable.

Certain embodiments of the present invention provide a sensor kit for home sleep diagnostic testing that by means of being pre-packaged and being pre-arranged in a compartmentalized tray or sealed pouch to provide the clinical sleep practitioner and the home sleep patient with a clean, safe and convenient means of providing a complete sensor kit for the appropriate level of sleep testing being prescribed.

In one embodiment, a sensor kit for a Type I sleep diagnostic testing included a thoracic (chest) effort belt, an abdominal effort belt, an oxygen saturation sensor, a nasal and oral airflow sensor, ECG electrodes, bipolar surface EMG electrodes, a triple EMG chin electrode, three EOG/ground electrodes, ten EEG electrodes and one neck snore sensor.

In another embodiment, a sensor kit for Type II sleep diagnostic testing includes a thoracic (chest) effort belt, an abdominal effort belt, an oxygen saturation sensor, a nasal and oral airflow sensor, ECG electrodes, a set of bipolar surface EMG electrodes, a triple EMG chin electrode, and set of three EOG/ground electrodes.

In another embodiment, a sensor kit for Type III sleep diagnostic testing includes a thoracic (chest) effort belt, an abdominal effort belt, an oxygen saturation sensor, a nasal and oral airflow sensor and a set of two ECG electrodes. In another embodiment, a sensor kit for Type IV sleep diagnostic testing includes only a thoracic (chest) effort belt, an abdominal effort belt, an oxygen saturation sensor and a nasal and oral airflow sensor.

In an example, a sensor kit is provided for diagnostic testing consisting of a compartmentalized tray or seal pouch and a multitude of sensors/electrodes that are used during sleep diagnostic testing. The kit may include a thoracic (chest) effort belt, an abdominal effort belt, an oxygen saturation sensor, a nasal and oral airflow sensor, ECG electrodes, a bipolar surface EMG electrode, a triple EMG chin electrode, three EOG/ground electrodes, ten EEG electrodes and one neck snore sensor, each type of device being stored in a different compartment of the tray or sealed pouch and optionally labeled to identify the electronic equipment each is to be used with.

In Example 1, a system for storing pre-packaged sleep related sensors and facilitating effective, efficient, or error-free usage of the sleep-related sensors for sleep diagnostic testing, the system including a receptacle configured to store sleep related sensors and a single set of sleep-related sensors. The single set of sleep-related sensors including a thoracic respiratory effort belt configured to detect chest movement indicative of respiratory effort, an abdominal respiratory effort belt configured to detect abdominal movement indicative of respiratory effort, an oxygen saturation sensor configured to an indication of blood oxygen saturation, and a nasal and oral airflow sensor configured to detect nasal and oral air flow information, wherein the receptacle includes instructions for using the thoracic respiratory effort belt, the abdominal effort belt, the oxygen saturation sensor, and the nasal and oral airflow sensor for sleep diagnostic testing.

In example 2, the single set of sleep-related sensors of Example 1 optionally includes a set of electrocardiogram (ECG) electrodes configured to sense electrical signals indicative of cardiac activity, and the receptacle of Example 1 optionally includes instructions for using the set of ECG electrodes for sleep diagnostic testing.

In Example 3, the single set of sleep-related sensors of any of Examples 1-2 optionally includes a set of electrocardiogram (ECG) electrodes configured to sense electrical signals indicative of cardiac activity, a set of bipolar surface electromyogram (EMG) electrodes configured to detect an indication of electrical activity of a muscle, and a triple EMG chin electrode configured to detect an indication of electrical activity at or near a chin, and the receptacle of any of Example 1-2 optionally includes instructions for using the set of EMG electrodes, the triple EMG chin electrode, and the set of EOG electrodes for sleep diagnostic testing.

In Example 4, the single set of sleep-related sensors of any of Examples 1-3 optionally includes a set of electroencephalogram (EEG) electrodes and the receptacle of any of Examples 1-3 optionally includes instructions for using the set of EEG electrodes for sleep diagnostic testing.

In example 5, the single set of sleep-related sensors of Example 1 consisting of the thoracic respiratory effort belt configured to detect chest movement indicative of respiratory effort, the abdominal respiratory effort belt configured to detect abdominal movement indicative of respiratory effort, the oxygen saturation sensor configured to an indication of blood oxygen saturation, and the nasal and oral airflow sensor configured to detect nasal and oral air flow information.

In Example 6, the single set of sleep-related sensors of Example 1 consisting of the thoracic respiratory effort belt configured to detect chest movement indicative of respiratory effort, the abdominal respiratory effort belt configured to detect abdominal movement indicative of respiratory effort, the oxygen saturation sensor configured to an indication of blood oxygen saturation, the nasal and oral airflow sensor configured to detect nasal and oral air flow information, and a set of electrocardiogram (ECG) electrodes configured to sense electrical signals indicative of cardiac activity, and the receptacle of Example 1 includes instructions for using the set of ECG electrodes for sleep diagnostic testing.

In Example 7, the single set of sleep-related sensors of Example 1 consisting of the thoracic respiratory effort belt configured to detect chest movement indicative of respiratory effort, the abdominal respiratory effort belt configured to detect abdominal movement indicative of respiratory effort, the oxygen saturation sensor configured to an indication of blood oxygen saturation, the nasal and oral airflow sensor configured to detect nasal and oral air flow information, a set of electrocardiogram (ECG) electrodes configured to sense electrical signals indicative of cardiac activity, a set of bipolar surface electromyogram (EMG) electrodes configured to detect an indication of electrical activity of a muscle, a triple EMG chin electrode configured to detect an indication of electrical activity at or near a chin, and a set of electrooculogram (EOG) electrodes configured to detect an indication of eye movement, and the receptacle of Example 1 includes instructions for using the set of ECG electrodes configured to detect an indication of electrical brain activity, the set of EMG electrodes, the triple EMG chin electrode, and the set of EOG electrodes for sleep diagnostic testing.

In Example 8, the single set of sleep-related sensors of Example 1 consisting of the thoracic respiratory effort belt configured to detect chest movement indicative of respiratory effort, the abdominal respiratory effort belt configured to detect abdominal movement indicative of respiratory effort, the oxygen saturation sensor configured to an indication of blood oxygen saturation, the nasal and oral airflow sensor configured to detect nasal and oral air flow information, a set of electrocardiogram (ECG) electrodes configured to sense electrical signals indicative of cardiac activity, a set of bipolar surface electromyogram (EMG) electrodes configured to detect an indication of electrical activity of a muscle, a triple EMG chin electrode configured to detect an indication of electrical activity at or near a chin, a set of electrooculogram (EOG) electrodes configured to detect an indication of eye movement, and a set of electroencephalogram (EEG) electrodes configured to detect an indication of electrical brain activity, and the receptacle of example 1 includes instructions for using the set of ECG electrodes, the set of EMG electrodes, the triple EMG chin electrode, the set of EOG electrodes, and the set of electroencephalogram (EEG) electrodes for sleep diagnostic testing.

In Example 9, the receptacle of any of Examples 1-8 optionally includes a pouch.

In Example 10, the receptacle of any of Examples 1-8 includes a compartmentalized tray.

In Example 11, a method for storing pre-packaged sleep related sensors to facilitate effective, efficient, or error-free usage of the sleep related sensors for sleep diagnostic testing includes storing a single set of sleep-related sensors in a receptacle and providing instructions with the receptacle for using the thoracic respiratory effort belt, the abdominal respiratory effort belt, the oxygen saturation sensor, and the nasal and oral airflow sensor. The step of storing the single set of sleep-related sensors includes storing a thoracic respiratory effort belt configured to detect chest movement indicative of respiratory effort, storing an abdominal respiratory effort belt configured to detect abdominal movement indicative of respiratory effort, storing an oxygen saturation sensor configured to an indication of blood oxygen saturation, and storing a nasal and oral airflow sensor configured to detect nasal and oral air flow information.

In Example 12, the storing the single set of sleep-related sensors in the receptacle of Example 11 optionally includes storing a set of electrocardiogram (ECG) electrodes configured to detect an indication of cardiac activity, and the method of Example 11 optionally includes providing instructions with the receptacle for using the ECG electrodes for sleep diagnostic testing.

In Example 13, the storing the single set of sleep-related sensors in the receptacle of any Examples of 11-12 optionally includes storing a set of bipolar surface electromyogram (EMG) electrodes configured to detect an indication of electrical activity of a muscle, storing a triple EMG chin electrode configured to detect an indication of electrical activity at or near a chin, and storing a set of electrooculogram (EOG) electrodes configured to detect an indication of eye movement, and the method of any of examples 11-12 optionally includes providing instructions with the receptacle for using the set of bipolar surface EMG electrodes, the triple EMG chin electrode, and the set of EOG electrodes for sleep diagnostic testing.

In Example 14, the storing the single set of sleep-related sensors in the receptacle of any of Examples 11-13 optionally includes storing a set of electroencephalogram (EEG) electrodes configured to detect an indication of electrical brain activity, and the method of any of Examples 11-13 optionally includes providing instructions for using the set of EEG electrodes for sleep diagnostic testing.

In Example 15, the storing the single set of sleep-related sensors in the receptacle of Example 11 consists of storing the thoracic respiratory effort belt configured to detect chest movement indicative of respiratory effort, storing the abdominal respiratory effort belt configured to detect abdominal movement indicative of respiratory effort, storing the oxygen saturation sensor configured to an indication of blood oxygen saturation, and storing the nasal and oral airflow sensor configured to detect nasal and oral air flow information.

In Example 16, the storing the single set of sleep-related sensors in the receptacle of Example 11 consists of storing the thoracic respiratory effort belt configured to detect chest movement indicative of respiratory effort, storing the abdominal respiratory effort belt configured to detect abdominal movement indicative of respiratory effort, storing the oxygen saturation sensor configured to an indication of blood oxygen saturation, storing the nasal and oral airflow sensor configured to detect nasal and oral air flow information, and storing a set of ECG electrodes configured to detect an indication of cardiac activity, and the method of Example 11 includes providing instructions with the receptacle for using the ECG electrodes for sleep diagnostic testing.

In Example 17, the storing the single set of sleep-related sensors in the receptacle of Example 11 consists of storing the thoracic respiratory effort belt configured to detect chest movement indicative of respiratory effort, storing the abdominal respiratory effort belt configured to detect abdominal movement indicative of respiratory effort, storing the oxygen saturation sensor configured to an indication of blood oxygen saturation, storing the nasal and oral airflow sensor configured to detect nasal and oral air flow information, and storing a set of ECG electrodes configured to detect an indication of cardiac activity, storing a set of bipolar surface electromyogram (EMG) electrodes configured to detect an indication of electrical activity of a muscle, storing a triple EMG chin electrode configured to detect an indication of electrical activity at or near a chin, and storing a set of electrooculogram (EOG) electrodes configured to detect an indication of eye movement, and the method of Example 11 includes providing instructions with the receptacle for using the ECG electrodes, the set of bipolar surface EMG electrodes, the triple EMG chin electrode, and the set of EOG electrodes for sleep diagnostic testing.

In Example 18, the storing the single set of sleep-related sensors in the receptacle of Example 11 consists of storing the thoracic respiratory effort belt configured to detect chest movement indicative of respiratory effort, storing the abdominal respiratory effort belt configured to detect abdominal movement indicative of respiratory effort, storing the oxygen saturation sensor configured to an indication of blood oxygen saturation, storing the nasal and oral airflow sensor configured to detect nasal and oral air flow information, and storing a set of ECG electrodes configured to detect an indication of cardiac activity, storing a set of bipolar surface electromyogram (EMG) electrodes configured to detect an indication of electrical activity of a muscle, storing a triple EMG chin electrode configured to detect an indication of electrical activity at or near a chin, storing a set of electrooculogram (EOG) electrodes configured to detect an indication of eye movement, and storing a set of electroencephalogram (EEG) electrodes configured to detect an indication of electrical brain activity, and the method of Example 11 includes providing instructions with the receptacle for using the ECG electrodes, the set of bipolar surface EMG electrodes, the triple EMG chin electrode, the set of EOG electrodes, and the set of EEG electrodes for sleep diagnostic testing.

In Example 19, the storing the single set of sleep-related sensors in the receptacle of any Examples 1-18 includes storing the single set of sleep-related sensors in a pouch.

In Example 20, the storing the single set of sleep-related sensors in the receptacle of any of Examples 11-18 includes storing the single set of sleep related sensors in a compartmentalized tray.

While the present disclosure is directed toward treatment of sleep disorders, further areas of applicability will become apparent from the description provided herein. It should be understood that the description and specific examples are intended for purposes of illustration only and are not intended to limit the scope of the present disclosure.

DESCRIPTION OF THE DRAWINGS

The forgoing features, objects and advantages of the invention will become apparent to those skilled in the art from the following detailed description, especially when considered in conjunction with the accompanying drawings in which like the numerals in the several views refer to the corresponding parts:

FIGS. 5A-D illustrate generally an example of a Type I & Type II sensor kit tray for sleep diagnostic testing.

DETAILED DESCRIPTION

The following detailed description relates to a sensor kit for sleep diagnostic testing. Each identified sensor kit is designed for sleep diagnostic testing directed toward treating patients with sleep disorders. The sleep sensors are adapted to be attached to patients during sleep studies in order to diagnose undesired sleep behavior or conditions obstructive sleep apnea, central sleep apnea, complex sleep apnea, snoring, restless leg syndrome (RLS), periodic limb movement (PLM), bruxism (teeth grinding and clenching), sudden infant death syndrome (SIDS) and other neurological disorders not necessarily related to sleep. The sensors transmit biomedical data to various types and levels of PSG machines.

The following detailed description includes discussion of the configuration of the sensor kit for sleep diagnostic testing. Additionally, molded trays containing the various sensor kits for a multitude of sleep diagnostic configurations are also included.

Figure 1:
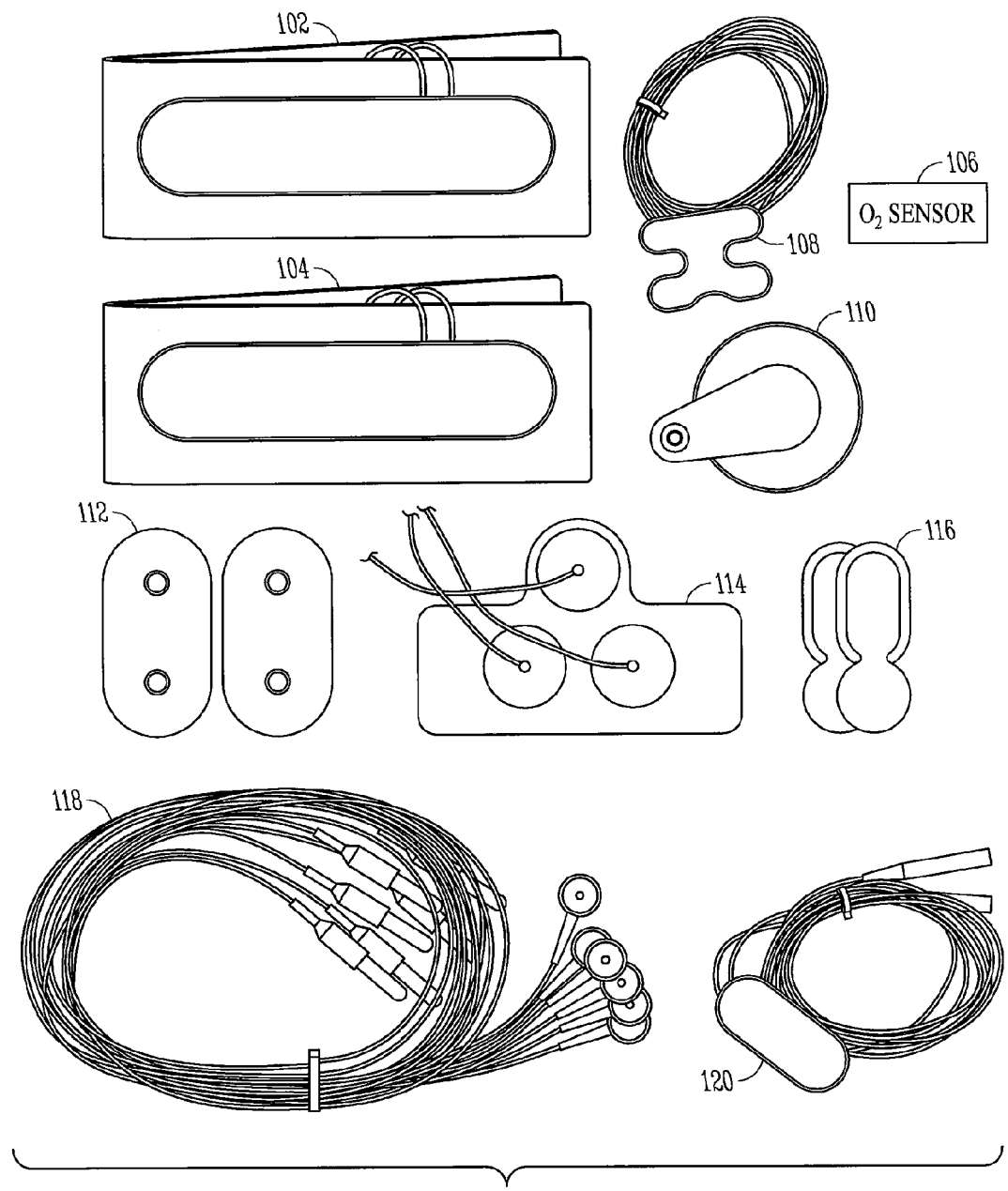
FIG. 1 illustrates generally an example of a Type I sensor kit for sleep diagnostic testing.

FIG. 1 illustrates generally an example of a Type I sensor kit for sleep diagnostic testing. Included are a thoracic (chest) effort belt 102, an abdominal effort belt 104, an oxygen saturation sensor 106, a nasal and oral airflow sensor 108, ECG electrodes 110, bipolar surface EMG electrodes 112, a triple EMG chin electrode 114, three EOG/ground electrodes 116, ten EEG electrodes 118 and one neck snore sensor 120.

The chest effort belt 102 and abdominal effort belt 104 are each body encircling bands having PVDF film transducers suitably mounted thereon so as to respond to stretching and relaxation of the belt due to the rise and fall of the chest and abdomen due to respiratory activity. The oxygen saturation sensor 106 is typically a finger clip having a set of infrared sources and sensors mounted thereon and adapted to be connected to a pulse oximeter by a cable. The nasal and oral air flow sensor 108 preferably comprises a PVDF film transducer sandwiched between layers of flexible plastic and having an adhesive thereon for adhering the transducer on the upper lip. A length of wire is used to connect the transducer element to a PSG machine. The ECG electrodes comprise any of a number of commercially available skin contacting electrodes that are adapted to snap on to leads (not shown) that connect to the ECG machine.

The EMG chin electrodes 114 are disposed on a flexible adhesive substrate that is adapted to adhere to the chin of a subject for detecting vibrations that may be caused by teeth grinding during sleep.

The EOG electrodes 116 are adapted to be placed on or about the subject's eye lids for sensing when the subject is in REM sleep mode.

The EEG electrodes 118, are commercially available and, as seen in FIG. 1, include surface electrodes connected by cabling to electrical terminals that are connectable to the EEG electronics module.

The snore sensor 120 comprises a PVDF piezoelectric transducer that is connectable by a length of cabling to the PSG electronics module and, in use, produces a signal indicative of throat vibrations present during episodes of snoring.

Figure 2:
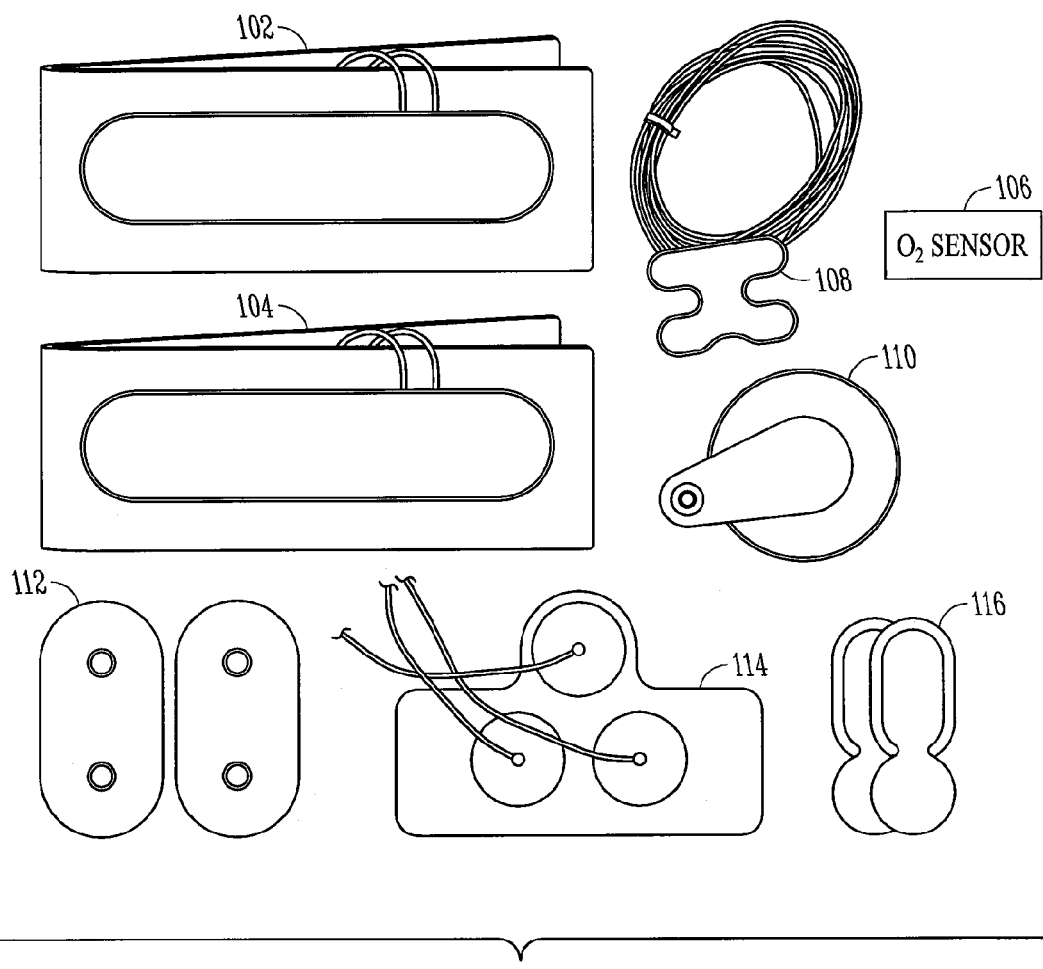
FIG. 2 illustrates generally an example of a Type II sensor kit for sleep diagnostic testing.

FIG. 2 illustrates generally an example of a Type II sensor kit for sleep diagnostic testing including a thoracic (chest) effort belt 102, an abdominal effort belt 104, an oxygen saturation sensor 106, a nasal and oral airflow sensor 108, ECG electrodes 110, a bipolar surface EMG electrode 112, a triple EMG chin electrode 114, and three EOG/ground electrodes 116.

Figure 3:
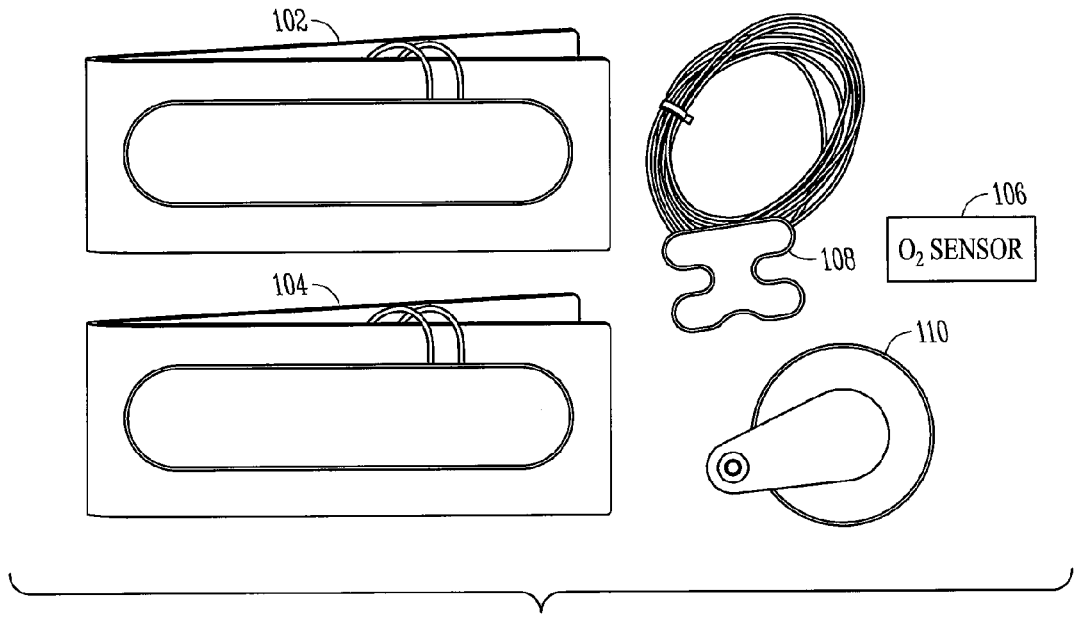
FIG. 3 illustrates generally an example of a Type III sensor kit for sleep diagnostic testing.

FIG. 3 illustrates generally an example of a Type III sensor kit for sleep diagnostic testing including a thoracic (chest) effort belt 102, an abdominal effort belt 104, an oxygen saturation sensor 106, a nasal and oral airflow sensor 108 and ECG electrodes 110.

Figure 4:
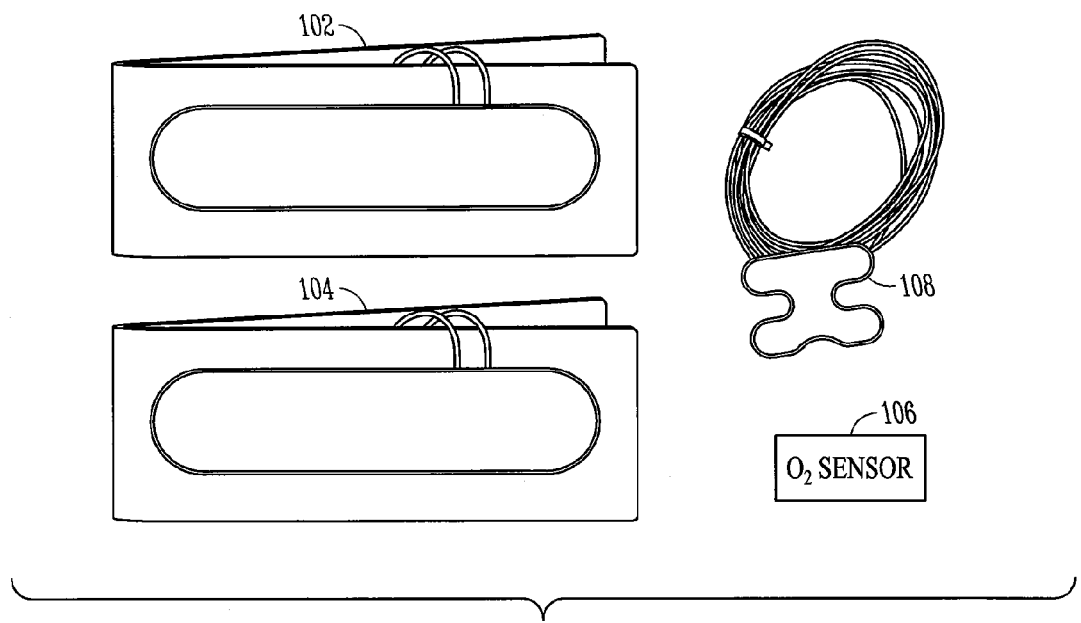
FIG. 4 illustrates generally an example of a Type IV sensor kit for sleep diagnostic testing.
Figure 6D:
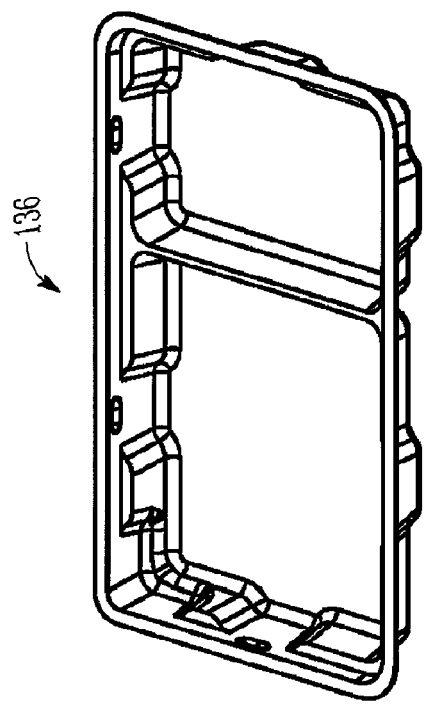
FIGS. 6A-D illustrate generally an example of a Type III & Type IV sensor kit tray for sleep diagnostic testing.
Figure 6A:
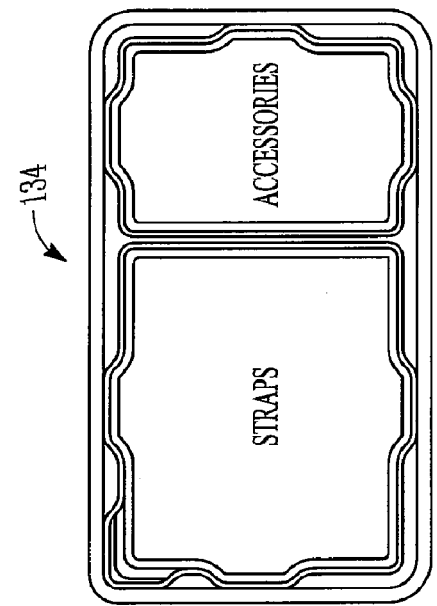
Figure 6B:
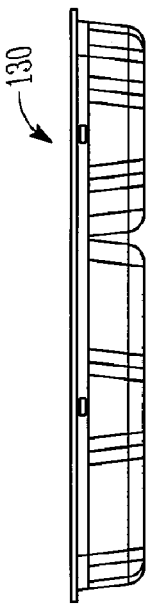
Figure 6C:
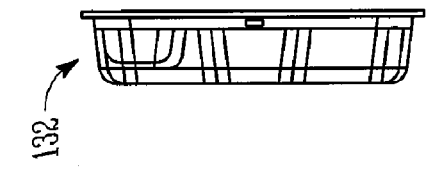

FIG. 4 illustrates generally an example of a Type IV sensor kit for sleep diagnostic testing including a thoracic (chest) effort belt 102, an abdominal effort belt 104, an oxygen saturation sensor 106 and a nasal and oral airflow sensor 108.

In an example, the nasal and oral airflow sensor 108 in FIG. 1 through 4 is a piezoelectric sensor constructed in accordance with the teachings of U.S. Pat. Nos. 5,311,875; 6,254,545; 6,485,432; 6,491,642, U.S. published application no. 2007/0012089 and U.S. Provisional Patent Application Ser. No. 61/075,136 filed Jun. 24, 2008 to Stasz and U.S. Pat. No. 6,894,427 to Alfini, the teachings of which are hereby incorporated by reference as if fully set forth herein.

In various embodiments, the effort belts 102 and 104 in FIG. 1 through 4 are effort belts in accordance with the teachings of U.S. application Ser. No. 11/743,389 filed May 3, 2007, the teachings of which are hereby incorporated by reference as if fully set forth herein.

FIGS. 5A-D illustrate generally an example front view 122, side view 126, rear view 124 and isometric view 126 of a Type I & Type II sensor kit tray. The tray is preferably formed in a suitable thermal forming process from a suitable medical grade thermo-plastic to create a plurality of divided compartments designed to segregate and store the several types of disposable sensors/electrodes during shipping and handling prior to uncovering at the time of use.

FIGS. 6A-D illustrate generally an example front view 130, side view 132, rear view 134 and isometric view 136 of a Type III & Type IV sensor kit tray. The trays shown in FIGS. 5A-D and 6A-D are illustrative only and may comprise greater or fewer numbers of compartments.

Those skilled in the art will understand and appreciate that various sleep diagnostic sensors include, but are not limited to, thermocouples, thermistors, piezo and pyroelectric transducers, air pressure transducers, electrodes, respiratory inductance plethysmography and respiratory effort plethysmography belts.

The systems or method incorporated herein are advantageous because it is directed toward the clean, safe, and practical use and application of all required sleep diagnostic sensors and/or electrodes in a single kit.

Additional advantages include time savings or convenience of having one pre-arranged sleep sensor kit containing all required sleep sensors for varying out the prescribed sleep diagnostic testing, which can provide a clean, safe, practical and convenient way to perform sleep diagnostic testing in either the sleep laboratory or home environment.

The present subject matter has been described herein in considerable detail to comply with the patent statutes and to provide those skilled in the art with the information needed to apply the novel principles and to construct and use such specialized components as are required. However, it is to be understood that the present subject matter can be carried out by specifically different equipment and devices, and that various modifications, both as to the equipment and operating procedures, can be accomplished without departing from the scope of the present subject matter.

The description of the various embodiments is merely exemplary in nature and, thus, variations that do not depart from the gist of the examples and detailed description herein are intended to be within the scope of the present disclosure. Such variations are not to be regarded as a departure from the spirit and scope of the present disclosure.

What is claimed is:

1. A system for storing pre-packaged sleep related sensors and facilitating effective, efficient, or error-free usage of the sleep related sensors for sleep diagnostic testing, the system comprising:
    a receptacle configured to store sleep related sensors; and
    a single set of sleep-related sensors, comprising:
    a thoracic respiratory effort belt configured to detect chest movement indicative of respiratory effort;
    an abdominal respiratory effort belt configured to detect abdominal movement indicative of respiratory effort;
    an oxygen saturation sensor configured to an indication of blood oxygen saturation; and
    a nasal and oral airflow sensor configured to detect nasal and oral air flow information;
    wherein the receptacle includes instructions for using the thoracic respiratory effort belt, the abdominal effort belt, the oxygen saturation sensor, and the nasal and oral airflow sensor for sleep diagnostic testing.

2. The system of claim 1, wherein the single set of sleep-related sensors includes a set of electrocardiogram (ECG) electrodes configured to sense electrical signals indicative of cardiac activity, and wherein the receptacle includes instructions for using the set of ECG electrodes for sleep diagnostic testing.

3. The system of claim 2, wherein the single set of sleep-related sensors include:
    a set of electrocardiogram (ECG) electrodes configured to sense electrical signals indicative of cardiac activity;
    a set of bipolar surface electromyogram (EMG) electrodes configured to detect an indication of electrical activity of a muscle; and
    a triple EMG chin electrode configured to detect an indication of electrical activity at or near a chin;
    wherein the receptacle includes instructions for using the set of EMG electrodes, the triple EMG chin electrode, and the set of ECG electrodes for sleep diagnostic testing.

4. The system of claim 3, wherein the single set of sleep-related sensors includes a set of electroencephalogram (EEG) electrodes, and wherein the receptacle includes instructions for using the set of EEG electrodes for sleep diagnostic testing.

5. The system of claim 1, wherein the single set of sleep-related sensors consists of:
    the thoracic respiratory effort belt configured to detect chest movement indicative of respiratory effort;
    the abdominal respiratory effort belt configured to detect abdominal movement indicative of respiratory effort;
    the oxygen saturation sensor configured to an indication of blood oxygen saturation; and
    the nasal and oral airflow sensor configured to detect nasal and oral air flow information.

6. The system of claim 1, wherein the single set of sleep-related sensors consists of
    the thoracic respiratory effort belt configured to detect chest movement indicative of respiratory effort;
    the abdominal respiratory effort belt configured to detect abdominal movement indicative of respiratory effort;
    the oxygen saturation sensor configured to an indication of blood oxygen saturation;
    the nasal and oral airflow sensor configured to detect nasal and oral air flow information; and
    a set of electrocardiogram (ECG) electrodes configured to sense electrical signals indicative of cardiac activity; and
    wherein the receptacle includes instructions for using the set of ECG electrodes for sleep diagnostic testing.

7. The system of claim 1, wherein the single set of sleep-related sensors consists of:
    the thoracic respiratory effort belt configured to detect chest movement indicative of respiratory effort;
    the abdominal respiratory effort belt configured to detect abdominal movement indicative of respiratory effort;
    the oxygen saturation sensor configured to an indication of blood oxygen saturation;
    the nasal and oral airflow sensor configured to detect nasal and oral air flow information;
    a set of electrocardiogram (ECG) electrodes configured to sense electrical signals indicative of cardiac activity;
    a set of bipolar surface electromyogram (EMG) electrodes configured to detect an indication of electrical activity of a muscle;
    a triple EMG chin electrode configured to detect an indication of electrical activity at or near a chin; and
    a set of electrooculogram (EOG) electrodes configured to detect an indication of eye movement; and
    wherein the receptacle includes instructions for using the set of ECG electrodes configured to detect an indication of electrical brain activity, the set of EMG electrodes, the triple EMG chin electrode, and the set of EOG electrodes for sleep diagnostic testing.

8. The system of claim 1, wherein the single set of sleep-related sensors consists of:
    the thoracic respiratory effort belt configured to detect chest movement indicative of respiratory effort;
    the abdominal respiratory effort belt configured to detect abdominal movement indicative of respiratory effort;
    the oxygen saturation sensor configured to an indication of blood oxygen saturation;
    the nasal and oral airflow sensor configured to detect nasal and oral air flow information;

a set of electrocardiogram (ECG) electrodes configured to sense electrical signals indicative of cardiac activity;
a set of bipolar surface electromyogram (EMG) electrodes configured to detect an indication of electrical activity of a muscle;
a triple EMG chin electrode configured to detect an indication of electrical activity at or near a chin;
a set of electrooculogram (EOG) electrodes configured to detect an indication of eye movement; and
a set of electroencephalogram (EEG) electrodes configured to detect an indication of electrical brain activity; and
wherein the receptacle includes instructions for using the set of ECG electrodes, the set of EMG electrodes, the triple EMG chin electrode, the set of EOG electrodes, and the set of electroencephalogram (EEG) electrodes for sleep diagnostic testing.

9. The system of claim 1, wherein the receptacle includes a pouch.

10. The system of claim 1, wherein the receptacle includes a compartmentalized tray.

11. A method for storing pre-packaged sleep related sensors to facilitate effective, efficient, or error-free usage of the sleep related sensors for sleep diagnostic testing, the method comprising:
storing a single set of sleep-related sensors in a receptacle, wherein storing the single set of sleep-related sensors comprises:
storing a thoracic respiratory effort belt configured to detect chest movement indicative of respiratory effort;
storing an abdominal respiratory effort belt configured to detect abdominal movement indicative of respiratory effort;
storing an oxygen saturation sensor configured to an indication of blood oxygen saturation; and
storing a nasal and oral airflow sensor configured to detect nasal and oral air flow information; and
providing instructions with the receptacle for using the thoracic respiratory effort belt, the abdominal respiratory effort belt, the oxygen saturation sensor, and the nasal and oral airflow sensor.

12. The method of claim 11, wherein the storing the single set of sleep-related sensors in the receptacle comprises storing a set of electrocardiogram (ECG) electrodes configured to detect an indication of cardiac activity; and
wherein the method includes providing instructions with the receptacle for using the ECG electrodes for sleep diagnostic testing.

13. The method of claim 12, wherein the storing the single set of sleep-related sensors in the receptacle includes:
storing a set of bipolar surface electromyogram (EMG) electrodes configured to detect an indication of electrical activity of a muscle;
storing a triple EMG chin electrode configured to detect an indication of electrical activity at or near a chin; and
storing a set of electrooculogram (EOG) electrodes configured to detect an indication of eye movement; and
wherein the method includes providing instructions with the receptacle for using the set of bipolar surface EMG electrodes, the triple EMG chin electrode, and the set of EOG electrodes for sleep diagnostic testing.

14. The method of claim 13, wherein the storing the single set of sleep-related sensors in the receptacle includes storing a set of electroencephalogram (EEG) electrodes configured to detect an indication of electrical brain activity; and
wherein the method includes providing instructions for using the set of EEG electrodes for sleep diagnostic testing.

15. The method of claim 11, wherein the storing the single set of sleep-related sensors in the receptacle consists of:
storing the thoracic respiratory effort belt configured to detect chest movement indicative of respiratory effort;
storing the abdominal respiratory effort belt configured to detect abdominal movement indicative of respiratory effort;
storing the oxygen saturation sensor configured to an indication of blood oxygen saturation; and
storing the nasal and oral airflow sensor configured to detect nasal and oral air flow information.

16. The method of claim 11, wherein the storing the single set of sleep-related sensors in the receptacle consists of:
storing the thoracic respiratory effort belt configured to detect chest movement indicative of respiratory effort;
storing the abdominal respiratory effort belt configured to detect abdominal movement indicative of respiratory effort;
storing the oxygen saturation sensor configured to an indication of blood oxygen saturation;
storing the nasal and oral airflow sensor configured to detect nasal and oral air flow information; and
storing a set of ECG electrodes configured to detect an indication of cardiac activity; and
wherein the method includes providing instructions with the receptacle for using the ECG electrodes for sleep diagnostic testing.

17. The method of claim 11, wherein the storing the single set of sleep-related sensors in the receptacle consists of:
storing the thoracic respiratory effort belt configured to detect chest movement indicative of respiratory effort;
storing the abdominal respiratory effort belt configured to detect abdominal movement indicative of respiratory effort;
storing the oxygen saturation sensor configured to an indication of blood oxygen saturation;
storing the nasal and oral airflow sensor configured to detect nasal and oral air flow information;
storing a set of electrocardiogram (ECG) electrodes configured to detect an indication of cardiac activity;
storing a set of bipolar surface electromyogram (EMG) electrodes configured to detect an indication of electrical activity of a muscle;
storing a triple EMG chin electrode configured to detect an indication of electrical activity at or near a chin; and
storing a set of electrooculogram (EOG) electrodes configured to detect an indication of eye movement; and
wherein the method includes providing instructions with the receptacle for using the ECG electrodes, the set of bipolar surface EMG electrodes, the triple EMG chin electrode, and the set of EOG electrodes for sleep diagnostic testing.

18. The method of claim 11, wherein the storing the single set of sleep-related sensors in the receptacle consists of:
storing the thoracic respiratory effort belt configured to detect chest movement indicative of respiratory effort;
storing the abdominal respiratory effort belt configured to detect abdominal movement indicative of respiratory effort;
storing the oxygen saturation sensor configured to an indication of blood oxygen saturation;
storing the nasal and oral airflow sensor configured to detect nasal and oral air flow information;

storing a set of electrocardiogram (ECG) electrodes configured to detect an indication of 1 cardiac activity;

storing a set of bipolar surface electromyogram (EMG) electrodes configured to detect an indication of electrical activity of a muscle;

storing a triple EMG chin electrode configured to detect an indication of electrical activity at or near a chin;

storing a set of electrooculogram (EOG) electrodes configured to detect an indication of eye movement; and storing a set of electroencephalogram (EEG) electrodes configured to detect an indication of electrical brain activity; and wherein the method includes providing instructions with the receptacle for using the ECG electrodes, the set of bipolar surface EMG electrodes, the triple EMG chin electrode, the set of EOG electrodes, and the set of EEG electrodes for sleep diagnostic testing.

19. The method of claim 11, wherein the storing the single set of sleep-related sensors in the receptacle includes storing the single set of sleep-related sensors in a pouch.

20. The method of claim 11, wherein the storing the single set of sleep-related sensors in the receptacle includes storing the single set of sleep related sensors in a compartmentalized tray.

* * * * *